(12) United States Patent
Pitkänen et al.

(10) Patent No.: US 11,966,509 B1
(45) Date of Patent: Apr. 23, 2024

(54) TRACKING PUPIL CENTRE DURING EYE SCANNING

(71) Applicant: Pixieray Oy, Espoo (FI)

(72) Inventors: Ari Pitkänen, Vantaa (FI); Klaus Melakari, Espoo (FI)

(73) Assignee: Pixieray Oy, Espoo (FI)

( * ) Notice: Subject to any disclaimer, the term of this patent is extended or adjusted under 35 U.S.C. 154(b) by 0 days.

(21) Appl. No.: 18/162,237

(22) Filed: Jan. 31, 2023

(51) Int. Cl.
*G09G 5/00* (2006.01)
*G06F 3/01* (2006.01)
*G02B 27/01* (2006.01)
*G02B 27/09* (2006.01)

(52) U.S. Cl.
CPC .......... *G06F 3/013* (2013.01); *G02B 27/0172* (2013.01); *G02B 27/0977* (2013.01)

(58) Field of Classification Search
CPC ......... G06F 3/013; G06F 3/012; G09G 3/001; G09G 2340/0464; G09G 2320/068; G09G 2354/00; G02B 27/0172; G02B 27/017; G02B 27/024; G02B 27/0977; G02B 27/0093; G02B 2027/0187; G02B 2027/0138
USPC .......................................................... 345/8
See application file for complete search history.

(56) References Cited

U.S. PATENT DOCUMENTS

| | | | |
|---|---|---|---|
| 2018/0157908 A1* | 6/2018 | Sahlsten | G02B 27/0172 |
| 2019/0187482 A1* | 6/2019 | Lanman | G02B 27/0179 |
| 2019/0258314 A1* | 8/2019 | Ollila | G02B 27/0172 |
| 2023/0169896 A1* | 6/2023 | Iwasaki | G06F 3/013 345/156 |

\* cited by examiner

*Primary Examiner* — Jennifer T Nguyen
(74) *Attorney, Agent, or Firm* — Ziegler IP Law Group

(57) ABSTRACT

An eye-tracking system (100, 302) comprises light source(s) (102, 202, 306); means (104, 200, 308) for changing direction of light beam (210) emitted by light source(s), wherein said means is to be employed to steer light beam to scan surface of user's eye (214); and light sensor(s) (106, 310) that is to be employed to sense reflected light signals. Said means is to be employed to detect when light beam is incident upon pupil of user's eye, based on variations in at least one parameter of reflected light signals; and steer light beam to be incident upon centre of pupil, wherein light beam is determined to be incident upon centre of pupil when minimum value from amongst values of at least one parameter of reflected light signals. Eye-tracking system further comprises processor(s) (108) configured to determine specific direction at which light beam is incident upon centre of pupil; determine position of pupil, based on specific direction, distance of pupil from light source(s), and position of light source(s); and determine gaze direction of user's eye.

20 Claims, 5 Drawing Sheets

TRACKING PUPIL CENTRE DURING EYE SCANNING

TECHNICAL FIELD

The present disclosure relates to eye-tracking systems. The present disclosure also relates to apparatuses implementing such eye-tracking systems. The present disclosure relates to methods for eye tracking.

BACKGROUND

In recent times, there has been rapid advancements in eye-tracking technology. Generally, the eye-tracking technology employs eye-tracking systems that detect and/or track a user's gaze within a visual scene in real time or near-real time. Such eye-tracking systems are being employed in various fields, such as immersive technologies, entertainment, medical imaging operations, simulators, navigation, and the like.

However, existing eye-tracking systems and methods for eye tracking are associated with several limitations. Firstly, some existing eye-tracking systems and methods involve use of multiple components (for example, such as optical components, electromechanical components, and the like) arranged in a complex manner. Integrating these multiple components in a required manner is quite challenging. This also makes apparatuses implementing such eye-tracking systems quite bulky and expensive. Secondly, some of the existing methods for eye tracking use complex processing techniques (for example, such as multiplexing, triangulation, and similar) that require high processing capabilities and thus, put a high computational burden on processing resources of the eye-tracking systems.

Therefore, in light of the foregoing discussion, there exists a need to overcome the aforementioned challenges associated with conventional eye-tracking systems and methods for eye tracking.

SUMMARY

The present disclosure seeks to provide an eye-tracking system. Moreover, the present disclosure also seeks to provide an apparatus implementing the eye-tracking system. Furthermore, the present disclosure also seeks to provide a method for eye tracking. An aim of the present disclosure is to provide a solution that overcomes at least partially the problems encountered in prior art.

In a first aspect, an embodiment of the present disclosure provides an eye-tracking system comprising:
  at least one light source;
  means for changing a direction of a light beam emitted by the at least one light source, wherein said means is to be employed to steer the light beam to scan a surface of a user's eye; and
  at least one light sensor that is to be employed to sense reflected light signals pertaining to reflections of the light beam off the surface of the user's eye,
wherein said means is to be employed to:
  detect when the light beam is incident upon a pupil of the user's eye during scanning of the surface of the user's eye, based on variations in at least one parameter of the reflected light signals sensed by the at least one light sensor during scanning; and
  steer the light beam to be incident upon a centre of the pupil, wherein the light beam is determined to be incident upon the centre of the pupil when a minimum value from amongst values of the at least one parameter of the reflected light signals is sensed by the at least one light sensor;
wherein the eye-tracking system further comprises at least one processor configured to:
  determine a specific direction of the light beam at which the light beam is incident upon the centre of the pupil;
  determine a position of the pupil of the user's eye, based on the specific direction of the light beam at which the light beam is incident upon the centre of the pupil, a distance of the pupil from the at least one light source, and a position of the at least one light source; and
  determine a gaze direction of the user's eye, based on the position of the pupil of the user's eye.

In a second aspect, an embodiment of the present disclosure provides an apparatus implementing the eye-tracking system of the first aspect, comprising at least one lens, wherein a first surface of the at least one lens is to face the user's eye when the apparatus is used by the user, wherein the at least one light source and the at least one light sensor are arranged along or in proximity of a periphery of the first surface of the at least one lens.

In a third aspect, an embodiment of the present disclosure provides a method for eye tracking, the method comprising:
  controlling at least one light source for emitting a light beam towards a user's eye;
  employing means for changing a direction of the light beam for steering the light beam to scan a surface of the user's eye;
  employing at least one light sensor for sensing reflected light signals pertaining to reflections of the light beam off the surface of the user's eye;
  detecting when the light beam is incident upon a pupil of the user's eye during scanning of the surface of the user's eye, based on variations in at least one parameter of the reflected light signals sensed by the at least one light sensor during scanning;
  steering the light beam to be incident upon a centre of the pupil, wherein the light beam is determined to be incident upon the centre of the pupil when a minimum value from amongst values of the at least one parameter of the reflected light signals is sensed by the at least one light sensor;
  determining a specific direction of the light beam at which the light beam is incident upon the centre of the pupil;
  determining a position of the pupil of the user's eye, based on the specific direction of the light beam at which the light beam is incident upon the centre of the pupil, a distance of the pupil from the at least one light source, and a position of the at least one light source; and
  determining a gaze direction of the user's eye, based on the position of the pupil of the user's eye.

Embodiments of the present disclosure substantially eliminate, or at least partially address the aforementioned problems in the prior art, and provide an eye-tracking system (and the method of eye-tracking) that simplifies an arrangement of components therein, that is cost-friendly and provides a faster and more accurate processing with limited processing resources.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
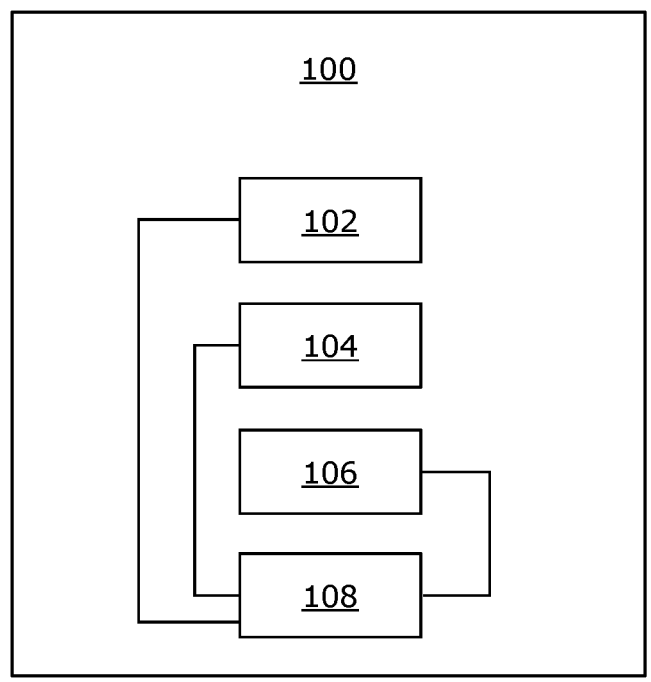
FIG. 1 illustrates a schematic diagram of an eye-tracking system, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify an item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In a first aspect, an embodiment of the present disclosure provides an eye-tracking system comprising:
at least one light source;
means for changing a direction of a light beam emitted by the at least one light source, wherein said means is to be employed to steer the light beam to scan a surface of a user's eye; and
at least one light sensor that is to be employed to sense reflected light signals pertaining to reflections of the light beam off the surface of the user's eye,
wherein said means is to be employed to:
detect when the light beam is incident upon a pupil of the user's eye during scanning of the surface of the user's eye, based on variations in at least one parameter of the reflected light signals sensed by the at least one light sensor during scanning; and
steer the light beam to be incident upon a centre of the pupil, wherein the light beam is determined to be incident upon the centre of the pupil when a minimum value from amongst values of the at least one parameter of the reflected light signals is sensed by the at least one light sensor;
wherein the eye-tracking system further comprises at least one processor configured to:
determine a specific direction of the light beam at which the light beam is incident upon the centre of the pupil;
determine a position of the pupil of the user's eye, based on the specific direction of the light beam at which the light beam is incident upon the centre of the pupil, a distance of the pupil from the at least one light source, and a position of the at least one light source; and
determine a gaze direction of the user's eye, based on the position of the pupil of the user's eye.

In a second aspect, an embodiment of the present disclosure provides an apparatus implementing the eye-tracking system of the first aspect, comprising at least one lens, wherein a first surface of the at least one lens is to face the user's eye when the apparatus is used by the user, wherein the at least one light source and the at least one light sensor are arranged along or in proximity of a periphery of the first surface of the at least one lens.

In a third aspect, an embodiment of the present disclosure provides a method for eye tracking, the method comprising:
controlling at least one light source for emitting a light beam towards a user's eye;
employing means for changing a direction of the light beam for steering the light beam to scan a surface of the user's eye;
employing at least one light sensor for sensing reflected light signals pertaining to reflections of the light beam off the surface of the user's eye;
detecting when the light beam is incident upon a pupil of the user's eye during scanning of the surface of the user's eye, based on variations in at least one parameter of the reflected light signals sensed by the at least one light sensor during scanning;
steering the light beam to be incident upon a centre of the pupil, wherein the light beam is determined to be incident upon the centre of the pupil when a minimum value from amongst values of the at least one parameter of the reflected light signals is sensed by the at least one light sensor;
determining a specific direction of the light beam at which the light beam is incident upon the centre of the pupil;
determining a position of the pupil of the user's eye, based on the specific direction of the light beam at which the light beam is incident upon the centre of the pupil, a distance of the pupil from the at least one light source, and a position of the at least one light source; and
determining a gaze direction of the user's eye, based on the position of the pupil of the user's eye.

The present disclosure provides the aforementioned eye-tracking system, the aforementioned apparatus, and the aforementioned method. The eye-tracking system and method facilitate a simple, yet accurate and reliable way to determine a gaze direction of a user's eye, in real time or near-real time. Herein, the eye-tracking system is easy to assemble and use, owing to use of very few components therein. Moreover, the eye-tracking system and method employ a simplified and efficient working principle, which reduces processing requirements of the eye-tracking system and the method as compared to existing eye-tracking systems and methods. Furthermore, the eye-tracking system and method is cost-friendly and works well even with limited processing resources. The apparatus implementing the eye-tracking system is lightweight and easy to use.

Throughout the present disclosure, the term "eye-tracking system" refers to a specialized equipment that is employed to detect and/or follow the user's eye for determining the gaze direction of the user's eye. It will be appreciated that the eye-tracking system is arranged in the apparatus in a manner that it does not cause any obstruction in a user's view. Thus, the apparatus utilizes the eye-tracking system for determining the gaze direction of the user's eye via non-invasive techniques. Moreover, an accurate tracking of the gaze direction may facilitate said apparatus to closely implement gaze contingency, for example, such as when presenting an extended-reality (XR) environment to the user, or in case of adaptive eyeglasses. The term "extended-reality" encompasses virtual reality (VR), augmented reality (AR), mixed reality (MR), and the like.

Throughout the present disclosure, the term "at least light source" refers to an equipment that, in operation, emits the light beam. Examples of the at least one light source include, but are not limited to, a light-emitting diode (LED), a projector, a display, a laser. The laser may be a vertical-cavity surface-emitting laser (VCSEL), an edge-emitting laser (EEL), and the like. Optionally, the light beams are infrared light beams. In other words, the at least one light source and the at least one light sensor optionally operate on infrared light and can be implemented as at least one infrared light source and at least one infrared light sensor. It will be appreciated that the infrared light beams (or near-infrared light beams) are invisible (or imperceptible) to a human eye, thereby, reducing unwanted distraction when such light beams are incident upon the user's eye. This subsequently facilitates in determining the gaze direction of the user's eye with high accuracy. Alternatively, optionally, the light beams are visible light beams. Yet alternatively, optionally, the light beams are ultraviolet light beams. In such a case, the at least one light source and the plurality of light sensors optionally operate on ultraviolet light and can be implemented as at least one ultraviolet light source and a plurality of ultraviolet light sensors. In this regard, ultraviolet light in a range of wavelengths that is not harmful to the human eye is selected. For example, a wavelength of the selected ultraviolet light may lie in a range of 315 nm to 400 nm.

Optionally, the at least one light source is implemented as a single light source. Beneficially, the presence of only the single light source in the eye-tracking system allows to design the eye-tracking apparatus in a simple manner, yet successfully and precisely scans the whole surface of the user's eye even with just the single light source.

Alternatively, optionally, the at least one light source is implemented as a plurality of light sources that are configured to emit the respective light beams to scan the surface of the user's eye. Optionally, the plurality of light sources are controlled to emit the respective light beams towards the user's eye by employing multiplexing. In such a case, operations of the plurality of light sources are interleaved and well-synchronized with each other, and thus do not interfere with each other. Moreover, such a multiplexing facilitates in simultaneously measuring of data from multiple directions, for example, using signal modulation and/or encoding. The multiplexing could comprise at least one of: time-division multiplexing, wavelength-division multiplexing, polarisation-division multiplexing, code-division multiplexing. The term "time-division multiplexing" refers to a time-based interleaving of the plurality of light sources, wherein a given light source emits the light beam towards the user's eye in a given time slot and/or at a given framerate only. The term "wavelength-division multiplexing" refers to a wavelength-based interleaving of the plurality of light sources, wherein different light sources have a capability to employ different wavelengths of light beams. Moreover, the term "polarisation-division multiplexing" refers to a polarisation-based interleaving of the plurality of light sources, wherein different light sources have a capability to employ different polarization states for emitting the light beam. Furthermore, the term "code-division multiplexing" refers to a code-based interleaving of the plurality of light sources, wherein different encoding is used to distinguish between different light sources that are operating simultaneously. The aforesaid multiplexing enables in determining which light source is used to scan the surface of the user's eye at a given moment of time.

Moreover, the aforesaid means is controlled to steer the light beam, i.e., to change an optical path of the light beam, for changing the direction of the light beam. The change in optical path of the light beam is implemented, for example, by reflection and/or refraction of the light beam, by steering of the at least one light source, and the like. Herein, the means is employed in order to ensure that the light beam is steered through a majority of the surface of the user's eye, and thus a complete scan of the surface of the user's eye is possible.

Optionally, said means is implemented as a liquid crystal optical element arranged in front of a light-emitting surface of the at least one light source. Optionally, in this regard, the liquid crystal optical element is electrically controlled by the at least one processor, to change the direction of the light beam emanating from the light-emitting surface of the at least one light source. In such a case, the at least one processor sends a drive signal to drive a control circuit of the liquid crystal optical element to control liquid-crystal molecules contained within the liquid crystal optical element, so as to change the direction of the light beam emanating from the light-emitting surface of the at least one light source. It will be appreciated that the liquid crystal optical element could be provided with different levels of drive signals to control molecular alignment (namely, orientation) of the liquid crystal molecules, thereby changing the direction of the light beam. Optionally, the liquid crystal optical element is implemented as a liquid crystal lens. This is because different molecular alignments of the liquid crystal molecules would result in different beam emission angles. Hence, the said means is easier to implement without any complex processing requirements.

Alternatively, optionally, said means is implemented as a micromirror arranged on an optical path of the light beam emitting from the at least one light source. Herein, the term "optical path" refers to a path through which the light beam travels after being emitted from the at least one light source. Herein, the term "micromirror" refers to a high-speed micro-electromechanical system (MEMS) based equipment that is used to steer the light beam (via reflection). The micromirror comprises multiple microscopically small mirrors that operate via an application of a voltage between two electrodes arranged around an array of the multiple microscopically small mirrors. Optionally, in this regard, the micromirror changes an orientation of a reflecting surface of the micromirror that lies in the optical path of the light beam that is emitted by the at least one light source, in order to change the direction of the light beam. Optionally, the at least one processor is configured to control the micromirror. Thus, implementing the said means as a micromirror provides individual control of each microscopically small mirror to precisely steer the light beam through entire surface of the user's eye. Moreover, the use of micromirror enables 2-dimensional steering of the light beam.

Yet alternatively, optionally, said means is implemented as an actuator that is employed to adjust an orientation of the at least one light source. Optionally, in this regard, the actuator changes an orientation of the at least one light source, so as to change the direction of the light beam emitted by the at least one light source. Optionally, the at least one processor is configured to control the actuator by way of an actuation signal. The actuation signal physically rotates and/or tilts the at least one light source to change the orientation of the at least one light source. Different rotations and/or tilts would result in different beam emission angles. The actuation signal could be, for example, an electrical signal, a hydraulic signal, a pneumatic signal, or similar. Herein, the term "actuator" refers to an equipment that is employed to rotate and/or tilt the at least one light source to which it is connected (directly or indirectly). Such an actuator may, for example, include electrical components, mechanical components, magnetic components, polymeric components, and the like. Hence, the said means is easier to implement.

Optionally, said means is configured to change the direction of the light beam during a time period between two consecutive emissions of the light beam by the at least one light source. In this regard, the direction of the light beam would remain the same during the emission of the light beam, i.e., the light beam does not appear to be (continuously) moving during the emission. In such a case, the reflections of the light beams off the surface of the user's eye for the two consecutive emissions would be sensed individually (i.e., the strength of the reflections would be measured separately for the two consecutive emissions). Hence, the gaze direction of the user's eye is determined for each separate emission.

Alternatively, optionally, said means is configured to change the direction of the light beam during emission of the light beam by the at least one light source. In this regard, the direction of the light beam would not remain the same during the emission, i.e., the light beam appears to be (continuously) moving during its emission as its direction is changing. In such a case, the reflections of the light beam off the surface of the user's eye would be sensed continuously (i.e., the strength of the reflections would be measured continuously). This beneficially allows for continuously scanning smaller sub-areas of the user's eye, thereby facilitating in determining the position of the pupil of the user's eye with a higher precision and a lower latency (i.e., in real time or near-real time, without any delay).

Throughout the present disclosure, the term "at least one light sensor" refers to an equipment that is operable to detect (namely, sense) the reflections of the light beams off the surface of the user's eye. Optionally, a given light sensor is implemented as at least one of: an IR light sensor, a visible light sensor, a UV light sensor.

In an example implementation, the at least one light source and the at least one light sensor are arranged at fixed positions in the eye-tracking system. For a given light source, only the direction of the light beam (that is emitted by the given light source) is changed to scan the user's eye.

It will be appreciated that the pupil of the user's eye moves according to a gaze direction of the user. Hence, it is essential to track the position of the pupil in order to determine the gaze direction of the user's eye. In this regard, the position of the pupil is indicative of the gaze direction.

Notably, when the at least one light source emits the light beam towards the user's eye, the light beam is incident upon different parts of the user's eye. Such parts of the user's eye could be, for example, such as an iris, a sclera, a pupil, and the like. In this regard, there might be an instant of time in which the light beam emitted by the at least one light source is incident upon the pupil of the user's eye. The specific direction of the light beam at said instant of time is detected based on the reflections. In this regard, the light signals that are reflected off the surface of the user's eye would have a number of parameters out of which the at least one parameter is sensed by the at least one light sensor. It will be appreciated that the value of the at least one parameter is almost constant when the light beam is incident upon different parts of an iris of the user's eye and the variation in the at least one parameter is sensed only when the light beam is incident upon the pupil of the user's eye after being incident on a part of the iris it just scanned.

Optionally, the at least one parameter of the reflected light signals comprises at least one of: light intensity, signal quality, signal-to-noise ratio. Herein, the term "light intensity" refers to an intensity of reflected light signal that is sensed by the at least one light sensor. Herein, the term "signal quality" refers to a quality of the reflected light signal. The signal quality could be used to detect if there is any attenuation present in the reflected light signal. Herein, the term "signal-to-noise ratio" refers to a measure of an amount of noise that is present in the reflected light signal.

When the light beam is incident upon the pupil after scanning a part of the iris, the value of the at least one parameter starts to decrease at a periphery on one side of the pupil and keeps on decreasing till the at least one parameter reaches the minimum value (i.e., when the light beam is incident upon the centre of the pupil). The value of the at least one parameter after reaching the minimum value, once again starts to increase as the light beam is steered from the centre of the pupil to the periphery on another side of the pupil. At this point, the light beam is steered backwards till the value of the at least one parameter of the reflected light reaches the minimum value for the at least one parameter, thus indicating that the light beam is incident upon the centre of the pupil.

Optionally, the light beam is detected to be incident upon the pupil when a value of the at least one parameter of the reflected light signals sensed by the at least one light sensor is a local minimum. Herein, the term "local minimum" refers to the value of the at least one parameter of the reflected signal reflected from a specific point of the user's eye that is having a lowest value in comparison to the values of the at least one parameter of the reflected signals reflected from neighbouring points of the specific point in the user's eye. Moreover, it is known that the value of the at least one parameter is less when the reflected signal is reflected from the pupil in comparison to the value of the at least one parameter of the reflected signals that are reflected from the other parts of the user's eye. Hence, if the value of the at least one parameter of the reflected signal is local minimum, then the light beam is detected to be incident upon the pupil.

Optionally, the light beam is detected to be incident upon the pupil when a value of the at least one parameter of the reflected light signals sensed by the at least one light sensor is attenuated by at least a predefined percent. In this regard, an amount of attenuation in the value of the at least one parameter for the reflected signal that is reflected from the pupil is much more than an amount of attenuation in the value of the at least one parameter for the reflected signal that is reflected from other parts of the user's eye. Hence, the light beam is detected to be incident upon the pupil when the value of the at least one parameter of the reflected light signal sensed by the at least one light sensor is attenuated by at least the predefined percentage. The predefined percent of attenuation is different for different parameters. For example, the predefined percent of attenuation for the light intensity may be at least 0.01 percent. The predefined percent of attenuation is based on a change in the value of the at least one parameter of the reflected light signal that is reflected from the pupil in comparison to the value of the at least one parameter of the reflected light signal that is reflected from the iris. The predefined percent (by which the reflected light signal should be attenuated to be considered to be incident upon the pupil) depends on encoding of a light signal. As an example, for an SNR of 70 decibels of a reflected light signal, the predefined percent could be as low as 0.1 percent. The SNR of 70 decibels means that 1 out of 10000000 would be detectable in the reflected light signal. An actual SNR may be at least 100 or 1000 times of 70 decibels, considering that there is absorbing light signal in the reflected light signal.

Moreover, optionally, the light beam is steered to be incident upon the centre of the pupil, based on an analysis of directions from which the reflected light signals have come towards the at least one light sensor within a predefined time period from an instant of time when the values of the at least one parameter of the reflected light signals started to increase after reaching the minimum value. In this regard, once it is detected that the minimum value is reached as the at least one parameter of the reflected light signals starts to increase once again after continuously decreasing, the instant of time at which the at last one parameter start to increase is taken as a reference for the predefined time period. Subsequently, based on the analysis of the directions from which the reflected light signals have come towards the at least one light sensor, an approximation about the position of the pupil of the user's eye is determined, which is then used to steer the light beam to be incident upon the centre of the pupil. For example, while scanning the surface of the user's eye from a left portion of the user's eye towards a right portion, if the at least one parameter of the reflected light signals starts to increase after reaching the minimum value, then the analysis of the directions of the reflected light signals (that have come towards the at least one light sensors during the predefined time period from the time instance after the minimum value is reached) is used to steer the light beam back from the right portion towards the left portion of the user's eye until a point is reached where the minimum value for the at least one parameter is reached. Optionally, the predefined time period may vary depending upon a speed with which the light beam is steered across the surface of the user's eye. Thus, beneficially, the light beam is precisely steered to be incident upon the centre of the pupil.

Optionally, the predefined time period is dynamic. That is, the value of predefined time period varies based on whether the gaze of the user's eye is tracked at a slower rate or at a higher rate based on an application for which the gaze direction of the user's eye is being tracked. Same light sensors could be used for both slow speed tracking and high speed tracking of the gaze direction of the user's eye. In an implementation scenario (for example, when the user is reading a book or watching a movie) that involves the slow speed tracking of the gaze direction of the user's eye and where the gaze direction of the user's eye is fixated at a point, the predefined time period could be in a range of 20 milliseconds to 900 milliseconds. In an alternative implementation scenario that involves the high speed tracking of the gaze direction of the user's eye for prediction and ballistic modelling of a movement of the user' eye, the predefined time period could be in a range of 20 microseconds to 500 microseconds; more optionally in a range of 20 microseconds to 100 microseconds.

In some implementations, the emission of the said light beam is implemented by using an analog signal feedback (for example, such as in servo control). Such an implementation is typically very fast, and is simple in construction. In such an implementation, a feedback measurement directly controls the actuators. In other implementations, the at least one processor may control an overall operation of the eye-tracking system. For this purpose, the at least one processor is at least communicably coupled to the at least one light source and to the means for changing the direction of the light beam, and the at least one light sensor. In such a case, said means is partly implemented by the at least one processor. It will be appreciated that the at least one processor may include a microcontroller or a microprocessor to control operations of the plurality of light sources and the plurality of light sensors.

Notably, the at least one processor uses the specific direction of the light beam at which the light beam is incident upon the centre of the pupil, the position of the at least one light source (i.e., at what position the at least one light source is present in the eye-tracking system), and the distance of the pupil from the at least light source, in order to determine the position of the pupil of the user's eye. For example, the position of the pupil of the user's eye may be determined to be towards a bottom left corner of the user's eye.

Optionally, the light beam is steered to scan the surface of the user's eye, based on a relative position of the at least one light source with respect to the user's eye. In this regard, the at least one light source is arranged at a fixed location in the eye-tracking apparatus (preferably at a periphery of the eye-tracking apparatus), thus an approximate position of the at least one light source is pre-known relative to the user's eye. Herein, even when an exact position of the at least one light source relative to the user's eye changes by a very small margin due to different eye configurations (e.g., different vertex distances, different interpupillary distances etc.) of different users, or due to a slight displacement as the user moves her/his head, the approximate position of the at least one light source relative to the user's eye still remains same (i.e., equal to the pre-known value). Hence, the relative position of the at least light source with respect to the user's eye is pre-known, and can be utilised to manoeuvre the light beam in the direction where the pupil can be detected.

Optionally, the at least one processor is configured to determine the distance of the pupil from the light source based on a time difference between time of emission by the at least one light source and time of sensing by the at least one light sensor. In this regard, a speed of light is pre-known and is used along with the time difference to determine the distance of the pupil from the light source. Advantageously, thus, the distance of the pupil from the light source is determined without a need for installing a separate sensor in the eye-tracking system.

Notably, different positions of the pupil correspond to different gaze directions of the user's eye. Once the position of the pupil is known to the at least one processor, the gaze direction of the user's eye can be easily determined by the at least one processor. As the pupil of the user's eye is oriented along the gaze direction of the user's eye, the (determined) position of the pupil enables the at least one processor to correctly determine the gaze direction of the user's eye. As an example, when the position of the pupil is towards a left side of the user's eye, the gaze direction of the user's eye is towards a left side of a field of view of the user's eye.

In this manner, the at least one processor could determine gaze directions of the user's eye based on some approximations, even without any calibration. Typically, human eyes can easily discern where a person's eye is gazing just by looking at the person's eye. Similarly, the at least one processor is configured to determine (approximate) gaze directions of the user's eye, just by knowing the position of the pupil of the user's eye. In some cases, it may be difficult to implement the calibration of the eye-tracking system for a particular user beforehand (i.e., prior to use of the eye-tracking system). Even in such cases, the at least one processor determines gaze directions of the user's eye based on the approximations.

Optionally, the at least one processor is configured to:
determine a correlation between different positions of the pupil and respective gaze directions of the user's eye, during an initial calibration of the eye-tracking system for the user's eye; and
utilise the correlation between the different positions of the pupil and the respective gaze directions of the user's eye, when determining the gaze direction of the user's eye.

In this regard, the gaze direction is determined from the position of the pupil, based on the correlation (between different positions of the pupil and different gaze directions), which is known beforehand. The correlation is determined during the initial calibration of the eye-tracking system. Advantageously, thus, the gaze direction of the user's eye is determined more accurately, without a need for any approximations.

In an example, during the initial calibration, the user may be required to wear a wearable device that comprises the eye-tracking system, and to view at least one reference image displayed on a display of the wearable device (or to view at least one reference image displayed on an external display through the wearable device). Herein, the term "reference image" refers to an image that is to be used for calibrating the eye-tracking system for the user's eye. Optionally, in this regard, the at least one reference image presents to the user a given visual target at a given location on the display or the external display. The term "visual target" refers to a visible mark that is represented within the at least one reference image and is distinctly visible in the at least one reference image. Different locations of the given visual target correspond to the different positions of the pupil and the respective gaze directions of the user's eye. The given visual target could be represented, for example, at a central portion, a corner portion, a top portion, a right side portion, a left side portion, and the like, within the at least one reference image. As an example, when the given visual target is at the central portion within the at least one reference image, the at least one processor could easily ascertain that the position of the pupil would be at a centre of the user's eye, and thus a gaze of the user's eye would be towards a central region of a field of view of the user's eye. As another example, when the given visual target is at the right side portion within the at least one reference image, the at least one processor could easily ascertain that the position of the pupil would be towards a right side of the user's eye, and thus the gaze direction of the user's eye would be towards a right side region of a field of view of the user's eye. Since the at least one processor controls displaying of the at least one reference image, the given location of the given visual target is already known to the at least one processor. In this regard, the at least one processor is configured to determine the correlation between the different positions of the pupil and the respective gaze directions of the user's eye, based on the given location of the given visual target. In this way, the at least one processor utilises the correlation for determining subsequent gaze directions of the user's eye. The wearable device could be, for example, such as an eye glass, a head-mounted display (HMD) device, and the like.

In another example, during the initial calibration, the user may be required to wear the wearable device comprising the eye-tracking system, and to focus on the given visual target represented within the at least one reference image while rotating his/her head. In yet another example, the calibration is not performed prior to using the eye-tracking system, but is performed during use of the wearable device comprising the eye-tracking system. In such a case, an initial error in the determined gaze direction may be high. Moreover, a machine learning model may be employed by the at least one processor to determine (and subsequently utilise) the correlation between the different positions of the pupil and the respective gaze directions of the user's eye.

Optionally, the at least one processor is configured to:
predict, based on a relative position of the at least one light sensor with respect to the user's eye, a direction from which the reflected light signals are expected to be incident upon the at least one light sensor after the light beam is reflected from the surface of the user's eye;
ignore any of the reflected light signals sensed by the at least one light sensor that do not correspond to the predicted direction from which the reflected light signals are expected to be incident;
select a remaining of the reflected light signals sensed by the at least one light sensor that correspond to the predicted direction from which the reflected light signals are expected to be incident; and
consider the values of the at least one parameter for only the selected remaining of the reflected light signals sensed by the at least one light sensor.

In this regard, the at least one light sensor receives reflected light signals from multiple directions in the environment in which the eye-tracking system is working. Herein, the at least one light sensor needs to only sense the reflected light signals that are reflected from the surface of the user's eye and ignore all other reflected light signals. Thus, the processor uses the relative position of the at least one light sensor to predict the direction from which the reflected light signals are expected to be incident upon the light sensor after being reflected from the surface of the user's eye. Subsequently, any of the reflected light signals that do not correspond to the predicted direction are ignored and the remaining of the reflected light signals that correspond to the predicted direction are selected for determining the position of the pupil. Hence, beneficially, only the reflected light signals from the surface of the user's eye are selected and utilised. This improves the accuracy of eye tracking.

The present disclosure also relates to the apparatus as described above. Various embodiments and variants disclosed above, with respect to the aforementioned first aspect, apply mutatis mutandis to the apparatus.

The apparatus implementing the eye-tracking system could be, for example, an eyeglass, a head-mounted display (HMD), a microscope, a telescope, a camera, or the like. Herein, the term "head-mounted display" device refers to an equipment that presents an extended-reality (XR) environment to a user when said HMD device, in operation, is worn by the user on his/her head. The HMD device is implemented, for example, as an XR headset, a pair of XR glasses, and the like, that is operable to display a visual scene of an XR environment to the user.

The at least one lens could be a concave lens, a convex lens, a bifocal lens, a liquid crystal lens, a Fresnel lens, a liquid crystal Fresnel lens or the like. Since eye tracking is to be performed for the user's eye when the apparatus is used by the user, the first surface of the at least one lens faces the user's eye. It will be appreciated that arranging the at least one light source and the at least one light sensor along or in the proximity of the periphery of the first surface of the at least one lens facilitates in emitting the light beam towards the user's eye, changing the directions of the light beams, and sensing the reflections of the light beams for accurate eye tracking.

The present disclosure also relates to the method of the second aspect as described above. Various embodiments and variants disclosed above, with respect to the aforementioned first aspect, apply mutatis mutandis to the method.

Optionally, the at least one parameter of the reflected light signals comprises at least one of: light intensity, signal quality, signal-to-noise ratio.

Optionally, the light beam is steered to scan the surface of the user's eye, based on a relative position of the at least one light source with respect to the user's eye.

Optionally, the method further comprises:
predicting, based on a relative position of the at least one light sensor with respect to the user's eye, a direction from which the reflected light signals are expected to be incident upon the at least one light sensor after the light beam is reflected from the surface of the user's eye;
ignoring any of the reflected light signals sensed by the at least one light sensor that do not correspond to the predicted direction from which the reflected light signals are expected to be incident;
selecting a remaining of the reflected light signals sensed by the at least one light sensor that correspond to the predicted direction from which the reflected light signals are expected to be incident; and
considering the values of the at least one parameter for only the selected remaining of the reflected light signals sensed by the at least one light sensor.

Optionally, the step of steering the light beam to be incident upon the centre of the pupil is performed based on an analysis of directions from which the reflected light signals have come towards the at least one light sensor within a predefined time period from an instant of time when the values of the at least one parameter of the reflected light signals started to increase after reaching the minimum value.

Optionally, the method further comprises:
determining a correlation between different positions of the pupil and respective gaze directions of the user's eye, during an initial calibration of the eye-tracking system for the user's eye; and
utilising the correlation between the different positions of the pupil and the respective gaze directions of the user's eye, when determining the gaze direction of the user's eye.

Optionally, the light beam is detected to be incident upon the pupil when a value of the at least one parameter of the reflected light signals sensed by the at least one light sensor is a local minimum.

Optionally, the light beam is detected to be incident upon the pupil when a value of the at least one parameter of the reflected light signals sensed by the at least one light sensor is attenuated by at least a predefined percent.

Optionally, the method further comprises determining the distance of the pupil from the light source based on a time difference between time of emission by the at least one light source and time of sensing by the at least one light sensor.

Optionally, said means is implemented as a liquid crystal optical element arranged in front of a light-emitting surface of the at least one light source. Alternatively, optionally, said means is implemented as a micromirror arranged on an optical path of the light beam emitting from the at least one light source. Yet alternatively, optionally, said means is implemented as an actuator that is employed for adjusting an orientation of the at least one light source.

Optionally, the direction of the light beam is changed during a time period between two consecutive emissions of the light beam by the at least one light source. Alternatively, optionally, the direction of the light beam is changed during emission of the light beam by the at least one light source.

DETAILED DESCRIPTION OF THE DRAWINGS

Referring to FIG. 1, illustrated is a schematic diagram of an eye-tracking system 100, in accordance with an embodiment of the present disclosure. The eye-tracking system 100 comprises at least one light source (depicted as a light source 102), a means 104 for changing a direction of a light beam emitted by the light source 102, at least one light sensor (depicted as a light sensor 106), and at least one processor (depicted as a processor 108). The processor 108 is coupled to the light source 102, the means 104, and the light sensor 106.

It may be understood by a person skilled in the art that FIG. 1 includes a simplified diagram of the eye-tracking system 100 for sake of clarity, which should not unduly limit the scope of the claims herein. The person skilled in the art will recognize many variations, alternatives, and modifications of embodiments of the present disclosure.

Figure 2A:
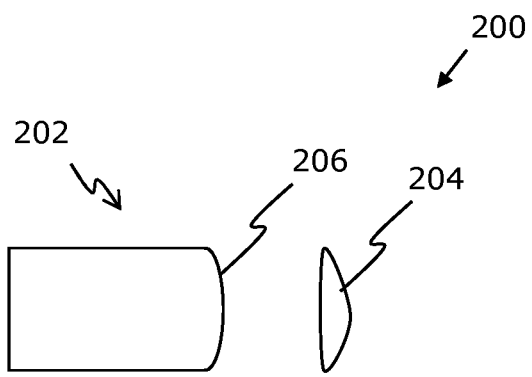
FIGS. 2A, 2B, and 2C illustrate implementations of a means for changing a direction of a light beam emitted by at least one light source, in accordance with various embodiments of the present disclosure.

Referring to FIG. 2A, illustrated is an implementation of a means 200 for changing a direction of a light beam emitted by at least one light source (depicted as a light source 202), in accordance with an embodiment of the present disclosure. The means 200 is implemented as a liquid crystal optical element 204 arranged in front of a light-emitting surface 206 of the light source 202. The liquid crystal optical element 204 is depicted, for example, as a liquid crystal lens.

Figure 2B:
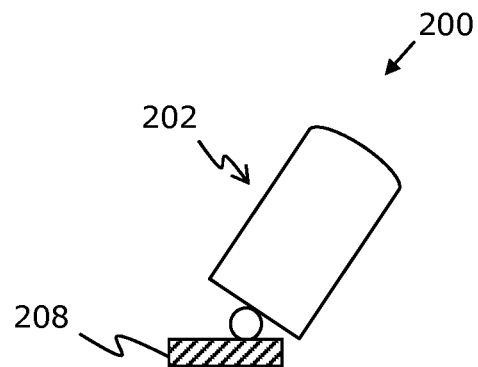

Referring to FIG. 2B, illustrated is another implementation of a means 200 for changing a direction of a light beam emitted by at least one light source (depicted as a light source 202), in accordance with another embodiment of the present disclosure. The means 200 is implemented as an actuator 208 that is employed to adjust an orientation of the light source 202. The actuator 208 is connected to the light source 202.

Figure 2C:
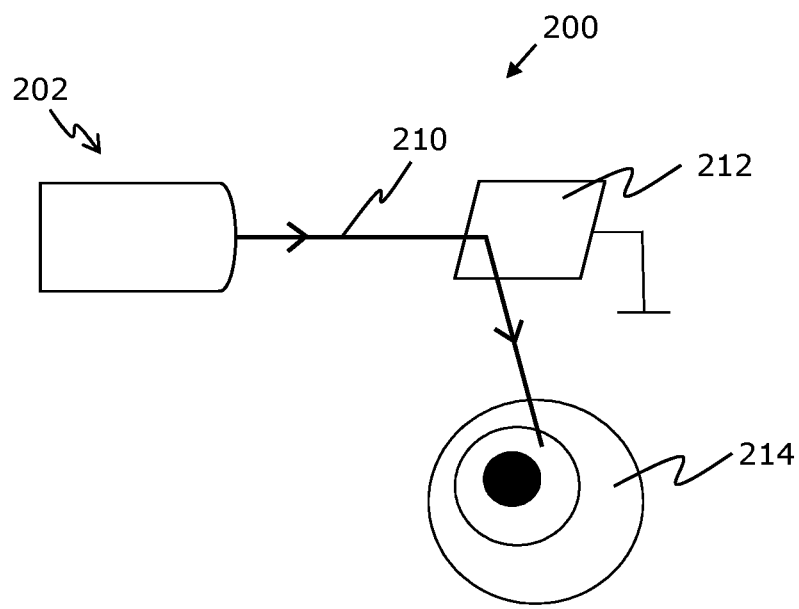

Referring to FIG. 2C, illustrated is yet another implementation of a means 200 for changing a direction of a light beam 210 emitted by at least one light source (depicted as a light source 202), in accordance with yet another embodiment of the present disclosure. The means 200 is implemented as a micromirror 212 arranged on an optical path of the light beam 210 emitting from the light source 202. The micromirror 212 is employed to adjust a direction of the light beam 210 that is emitted from the light source 202 towards a user's eye 214.

It may be understood by a person skilled in the art that FIGS. 2A, 2B and 2C include simplified implementations of the means 200 for sake of clarity, which should not unduly limit the scope of the claims herein. The person skilled in the art will recognize many variations, alternatives, and modifications of embodiments of the present disclosure.

Figure 3:
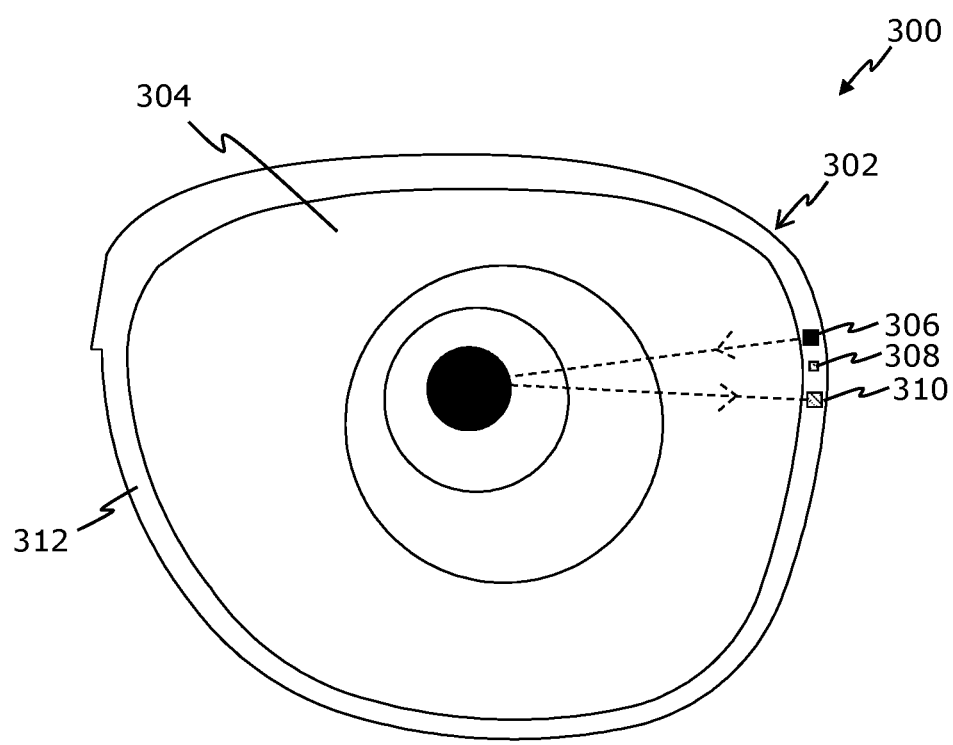
FIG. 3 is a schematic diagram of a portion of an apparatus in which an eye-tracking system is implemented, in accordance with an embodiment of the present disclosure.

Referring to FIG. 3, illustrated is a schematic diagram of a portion of an apparatus 300 in which an eye-tracking system 302 is implemented, in accordance with an embodiment of the present disclosure. The apparatus 300 comprises at least one lens (depicted as a lens 304), wherein a first surface of the at least one lens is to face a user's eye when the apparatus is used by the user. The eye-tracking system 302 comprises at least one light source (depicted as a light source 306 shown as a solid square), a means (depicted as a means 308 shown as a smaller square) for changing a direction of a light beam emitted by the light source 306, at least one light sensor (depicted as a light sensor 310 shown as a slanted-hatched square), and at least one processor (not shown).

The at least one light source, the means, the at least one light sensor, and at least one processor of the eye-tracking system 302 are arranged along or in proximity of a periphery 312 of the first surface of the at least one lens, as shown.

FIG. 3 is merely an example, which should not unduly limit the scope of the claims herein. The person skilled in the art will recognize many variations, alternatives, and modifications of embodiments of the present disclosure.

Figure 4A:
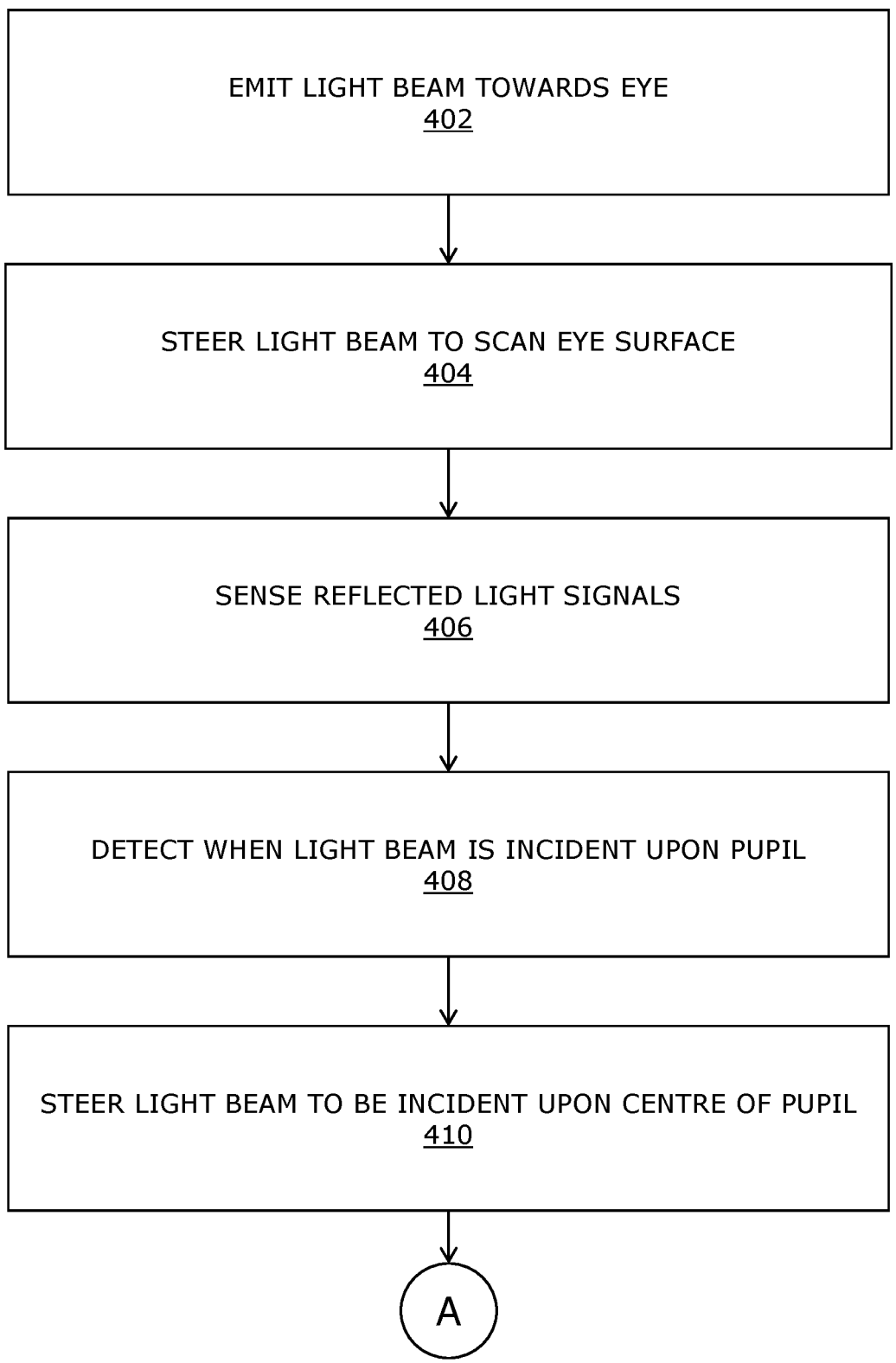
FIGS. 4A and 4B collectively illustrate steps of a method for eye tracking, in accordance with an embodiment of the present disclosure.
Figure 4B:
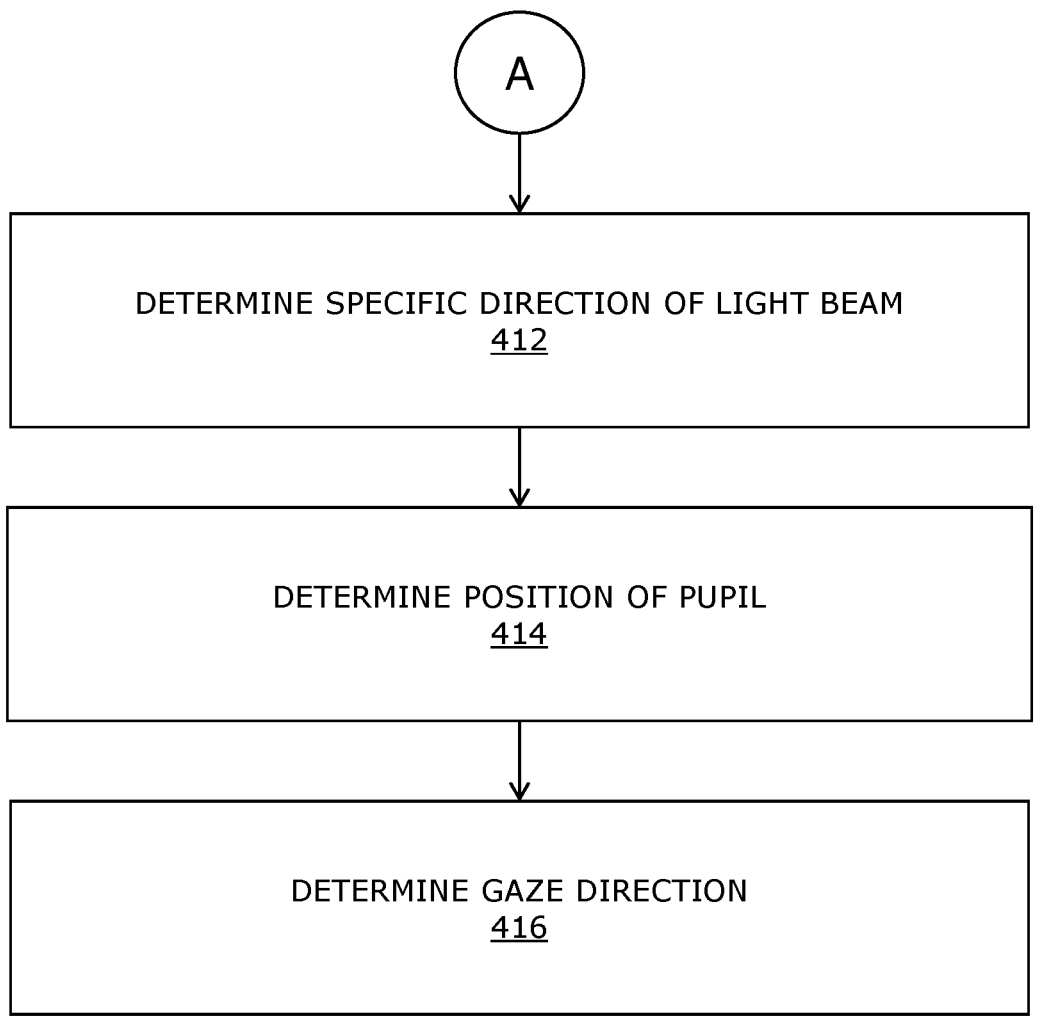

Referring to FIGS. 4A and 4B, illustrated are steps of a method for eye tracking, in accordance with an embodiment of the present disclosure. At step 402, at least one light source is controlled for emitting a light beam towards a user's eye. At step 404, means for changing a direction of the light beam is employed for steering the light beam to scan a surface of the user's eye. At step 406, at least one light sensor is employed for sensing reflected light signals pertaining to reflections of the light beam off the surface of the user's eye. At step 408, it is detected when the light beam is incident upon a pupil of the user's eye, during scanning of the surface of the user's eye, based on variations in at least one parameter of the reflected light signals sensed by the at least one light sensor during scanning. At step 410, the light beam is steered to be incident upon a centre of the pupil, wherein the light beam is determined to be incident upon the centre of the pupil when a minimum value from is amongst values of the at least one parameter of the reflected light signals is sensed by the at least one light sensor. At step 412, a specific direction of the light beam at which the light beam is incident upon the centre of the pupil is determined. At step 414, a position of the pupil of the user's eye is determined, based on the specific direction of the light beam at which the light beam is incident upon the centre of the pupil, a distance of the pupil from the at least one light source, and a position of the at least one light source. At step 416, a gaze direction of the user's eye is determined, based on the position of the pupil of the user's eye.

The aforementioned steps are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural. It will be appreciated that the terms "first", "second", "third" and the like used herein do not denote any order, quantity or importance, but rather are used to distinguish one element from another.

The invention claimed is:

1. An eye-tracking system comprising:
   at least one light source;
   means for changing a direction of a light beam emitted by the at least one light source, wherein said means is to be employed to steer the light beam to scan a surface of a user's eye; and
   at least one light sensor that is to be employed to sense reflected light signals pertaining to reflections of the light beam off the surface of the user's eye,
   wherein said means is to be employed to:
      detect when the light beam is incident upon a pupil of the user's eye during scanning of the surface of the user's eye, based on variations in at least one parameter of the reflected light signals sensed by the at least one light sensor during scanning; and
      steer the light beam to be incident upon a centre of the pupil, wherein the light beam is determined to be incident upon the centre of the pupil when a minimum value from amongst values of the at least one parameter of the reflected light signals is sensed by the at least one light sensor;
   wherein the eye-tracking system further comprises at least one processor configured to:
      determine a specific direction of the light beam at which the light beam is incident upon the centre of the pupil;
      determine a position of the pupil of the user's eye, based on the specific direction of the light beam at which the light beam is incident upon the centre of the pupil, a distance of the pupil from the at least one light source, and a position of the at least one light source; and
      determine a gaze direction of the user's eye, based on the position of the pupil of the user's eye.

2. The eye-tracking system of claim 1, wherein the at least one parameter of the reflected light signals comprises at least one of: light intensity, signal quality, signal-to-noise ratio.

3. The eye-tracking system of claim 1, wherein the light beam is steered to scan the surface of the user's eye, based on a relative position of the at least one light source with respect to the user's eye.

4. The eye-tracking system of claim 1, wherein the at least one processor is configured to:
   predict, based on a relative position of the at least one light sensor with respect to the user's eye, a direction from which the reflected light signals are expected to be incident upon the at least one light sensor after the light beam is reflected from the surface of the user's eye;
   ignore any of the reflected light signals sensed by the at least one light sensor that do not correspond to the predicted direction from which the reflected light signals are expected to be incident;
   select a remaining of the reflected light signals sensed by the at least one light sensor that correspond to the predicted direction from which the reflected light signals are expected to be incident; and
   consider the values of the at least one parameter for only the selected remaining of the reflected light signals sensed by the at least one light sensor.

5. The eye-tracking system of claim 1, wherein the light beam is steered to be incident upon the centre of the pupil, based on an analysis of directions from which the reflected light signals have come towards the at least one light sensor within a predefined time period from an instant of time when the values of the at least one parameter of the reflected light signals started to increase after reaching the minimum value.

6. The eye-tracking system of claim 1, wherein the at least one processor is configured to:
determine a correlation between different positions of the pupil and respective gaze directions of the user's eye, during an initial calibration of the eye-tracking system for the user's eye; and
utilise the correlation between the different positions of the pupil and the respective gaze directions of the user's eye, when determining the gaze direction of the user's eye.

7. The eye-tracking system of claim 1, wherein the light beam is detected to be incident upon the pupil when a value of the at least one parameter of the reflected light signals sensed by the at least one light sensor is a local minimum.

8. The eye-tracking system of claim 1, wherein the light beam is detected to be incident upon the pupil when a value of the at least one parameter of the reflected light signals sensed by the at least one light sensor is attenuated by at least a predefined percent.

9. The eye-tracking system of claim 1, wherein the at least one processor is configured to determine the distance of the pupil from the light source based on a time difference between time of emission by the at least one light source and time of sensing by the at least one light sensor.

10. The eye-tracking system of claim 1, wherein said means is implemented as a liquid crystal optical element arranged in front of a light-emitting surface of the at least one light source.

11. The eye-tracking system of claim 1, wherein said means is implemented as a micromirror arranged on an optical path of the light beam emitting from the at least one light source.

12. The eye-tracking system of claim 1, wherein said means is implemented as an actuator that is employed to adjust an orientation of the at least one light source.

13. The eye-tracking system of claim 1, wherein said means is configured to change the direction of the light beam during a time period between two consecutive emissions of the light beam by the at least one light source.

14. The eye-tracking system of claim 1, wherein said means is configured to change the direction of the light beam during emission of the light beam by the at least one light source.

15. An apparatus implementing the eye-tracking system of claim 1, comprising at least one lens, wherein a first surface of the at least one lens is to face the user's eye when the apparatus is used by the user, wherein the at least one light source and the at least one light sensor are arranged along or in proximity of a periphery of the first surface of the at least one lens.

16. A method for eye tracking, the method comprising:
controlling at least one light source for emitting a light beam towards a user's eye;
employing means for changing a direction of the light beam for steering the light beam to scan a surface of the user's eye;
employing at least one light sensor for sensing reflected light signals pertaining to reflections of the light beam off the surface of the user's eye;
detecting when the light beam is incident upon a pupil of the user's eye during scanning of the surface of the user's eye, based on variations in at least one parameter of the reflected light signals sensed by the at least one light sensor during scanning;
steering the light beam to be incident upon a centre of the pupil, wherein the light beam is determined to be incident upon the centre of the pupil when a minimum value from amongst values of the at least one parameter of the reflected light signals is sensed by the at least one light sensor;
determining a specific direction of the light beam at which the light beam is incident upon the centre of the pupil;
determining a position of the pupil of the user's eye, based on the specific direction of the light beam at which the light beam is incident upon the centre of the pupil, a distance of the pupil from the at least one light source, and a position of the at least one light source; and
determining a gaze direction of the user's eye, based on the position of the pupil of the user's eye.

17. The method of claim 16, wherein the light beam is steered to scan the surface of the user's eye, based on a relative position of the at least one light source with respect to the user's eye.

18. The method of claim 16, further comprising:
predicting, based on a relative position of the at least one light sensor with respect to the user's eye, a direction from which the reflected light signals are expected to be incident upon the at least one light sensor after the light beam is reflected from the surface of the user's eye;
ignoring any of the reflected light signals sensed by the at least one light sensor that do not correspond to the predicted direction from which the reflected light signals are expected to be incident;
selecting a remaining of the reflected light signals sensed by the at least one light sensor that correspond to the predicted direction from which the reflected light signals are expected to be incident; and
considering the values of the at least one parameter for only the selected remaining of the reflected light signals sensed by the at least one light sensor.

19. The method of claim 16, wherein the step of steering the light beam to be incident upon the centre of the pupil is performed based on an analysis of directions from which the reflected light signals have come towards the at least one light sensor within a predefined time period from an instant of time when the values of the at least one parameter of the reflected light signals started to increase after reaching the minimum value.

20. The method of claim 16, wherein further comprising determining the distance of the pupil from the light source based on a time difference between time of emission by the at least one light source and time of sensing by the at least one light sensor.

* * * * *